United States Patent [19]

Yonemitsu et al.

[11] 3,953,529

[45] Apr. 27, 1976

[54] PROCESS FOR ORTHO-ALKYLATION OF PHENOL COMPOUNDS

[75] Inventors: Eiichi Yonemitsu, Kashiwa; Shizuo Togo, Tokyo; Kenichiro Hashimoto, Tokyo; Muneo Ito, Tokyo; Chiharu Nishizawa, Tokyo; Noboru Hara, Tokyo, all of Japan

[73] Assignee: Mitsubishi Gas Chemical Co. Inc., Tokyo, Japan

[22] Filed: June 4, 1974

[21] Appl. No.: 476,268

[30] Foreign Application Priority Data
June 12, 1973 Japan.............................. 48-66025
Aug. 16, 1973 Japan.............................. 48-01894

[52] U.S. Cl............................ 260/621 R; 260/620; 260/624 C
[51] Int. Cl.².................. C07C 39/06; C07C 39/12
[58] Field of Search........ 260/621 R, 624 R, 624 C, 260/620

[56] References Cited
UNITED STATES PATENTS
2,448,942  9/1948  Winkler et al.................. 260/624 C
3,716,589  2/1973  Kotanigawa et al............ 260/624 C FOREIGN PATENTS OR APPLICATIONS
717,588  10/1954  United Kingdom............. 260/621 R
749,422  12/1966  Canada........................... 260/621 R Primary Examiner—James O. Thomas, Jr.
Assistant Examiner—W. B. Lone
Attorney, Agent, or Firm—Sherman & Shalloway

[57] ABSTRACT

A process for alkylating the ortho-position of a phenol compound which comprises bringing a phenol compound containing at least one hydrogen atom at its ortho-position and an alcohol into contact with a catalyst in the gaseous phase, said catalyst being selected from the group consisting of
a. a mixture of iron oxide and silica in which the atomic ratio of Fe to Si is 100 : 0.03 – 200, and
b. a mixture of iron oxide, silica and chromium oxide in which the atomic ratio of Fe to Si to Cr is 100 : 0.1 – 5 : 0.1 – 5.

8 Claims, No Drawings

PROCESS FOR ORTHO-ALKYLATION OF PHENOL COMPOUNDS

This invention relates to a process for selectively alkylating the ortho-position of phenol compounds.

Phenol compounds with alkylated ortho-position are useful as various industrial materials. For example, 2,6-xylenol is used as a material for polyphenylene ether.

A method has already been known to alkylate the ortho-position of a phenol compound by catalytically reacting the phenol compound with an alcohol. When, for example, it is desired to obtain a 2,6-dialkyl phenol, para-substitution products, such as para-alkylphenol, 2,4-dialkylphenol or 2,4,6-trialkyl phenol, are formed as by-products. These by-products are difficult to separate from the 2,6-dialkylphenol, and therefore, it is important to inhibit the formation of these by-products as much as possible by raising the selectivity of the reaction.

The conventional processes are all disadvantageous for commercial operation because the selectivity is low or the yield of the product is low. Furthermore, some of them have the defect that the durability of the catalytic activity is low and a fresh catalyst should be charged frequently.

For example, U.S. Pat. No. 2,448,942 discloses a process for methylating a phenol compound using a metal oxide, especially aluminum oxide. However, this process is suitable for obtaining phenol compounds substituted by 3 or more alkyl groups, and the selectivity of the alkylation of the ortho-position is low.

British Pat. No. 717,588 discloses a process for preparing 2,6-xylenol by alkylating o-cresol with methanol using a metal oxide, preferably aluminum oxide, as a catalyst. However, according to this process, the conversion of o-cresol and the selectivity to 2,6-xylenol are very low.

There was also proposed a process for producing 2,6-xylenol by methylating phenol using magnesium oxide as a catalyst. Since this process requires high temperatures, the catalytic activity gradually decreases by the deposition of a carbonaceous substance, and the growth of the crystallites of magnesium causes an irreversible reduction in its activity, which in turn leads to the neccessity of exchanging the catalyst after a short period of time.

It has also been known to use iron oxide as a catalyst, but since it inherently has a low catalytic activity and the activity decreases abruptly, this method has not been utilized commercially. In an attempt to remove these defects of the iron oxide catalyst, a method has been proposed in which a mixture of iron oxide and zinc oxide is used as a catalyst (Japanese Pat. Publication No. 37812/71). In this method, too, the activity of the catalyst is not sufficient, and especially its durability is unsatisfactory.

It is an object of this invention to provide a process for alkylating the ortho-position of a phenol compound by catalytically reacting the phenol compound with an alcohol, and which permits the preparation of an ortho-alkylated phenol at high selectively and high yield and good maintenance of the activity and selectivity of the catalyst for prolonged period of time, as compared with the conventional processes.

According to the present invention, there is provided a process for alkylating the ortho-position of a phenol compound which comprises bringing a phenol compound containing at least one hydrogen atom at its orthoposition and an alcohol into contact with a catalyst in the gaseous phase, said catalyst being selected from the group consisting of a. a mixture of iron oxide and silica in which the atomic ratio of Fe to Si is 100 : 0.03 – 200, and b. a mixture of iron oxide, silica and chromium oxide in which the atomic ratio of Fe to Si to Cr is 100 : 0.1 – 5 : 0.1 – 5.

In view of the fact that good results cannot be obtained with the use of iron oxide and silica either alone or a mixture of iron oxide and chromium oxide, it is surprising and unexpected that the use of the catalyst (a) or (b) specified in the present invention gives superior results in all of the selectivity, the yield, and the durability of activity.

The phenol compound containing at least one hydrogen atom at the ortho-position as used in the present invention is expressed by the following general formula (I)

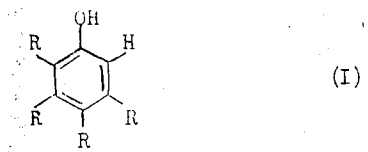

wherein R's may be the same or different, and each represent a monovalent substituent, such as a hydrogen atom, an alkyl group, or a phenyl group.

Examples of the compounds of the formula (I) are phenol, orthocresol, meta-cresol, para-cresol, 2,3-xylenol, 2,4-xylenol, 2,5-xylenol, 3,5-xylenol, 3,4-xylenol, 2,3,4-trimethylphenol, 2,3,5-trimethylphenol, 2,4,5-trimethyl phenol, 2,3,4,5-tetramethylphenol, ortho-ethylphenol, metaethylphenol, para-ethylphenol, 2,3-diethylphenol, 2,4-diethylphenol, 2,5-diethylphenol, 3,5-diethylphenol, 3,4-diethylphenol, 2,3,4-triethylphenol, 2,4,5-triethylphenol, ortho-propylphenol, ortho-phenylphenol, paraphenylphenol, ortho-cyclohexylphenol, and para-cyclohexylphenol.

Examples of the alcohols used in this invention are lower saturated aliphatic alcohols containing 1 to 4 carbon atoms. Ethanol, and especially methanol, are preferred.

The catalyst used in this invention is either (a) or (b) shown below.

The catalyst (a) is a mixed catalyst consisting of iron oxide and silica in which the atomic ratio of Fe to Si is 100 : 0.03 – 200, preferably 100 : 0.1 – 50. If the ratio of Si is greater than 200, the activity and selectivity of the catalyst are reduced to increase the proportion of paraalkyl substitution products and alkylphenyl ethers formed as by-products. If the proportion of Si is less than 0.03, the activity of the catalyst is low, and the time for maintaining the activity becomes shorter. The iron oxide is effective in any form such as $Fe_2O_3$, $Fe_3O_4$, and $FeO$.

The catalyst (b) is a mixed catalyst consisting of iron oxide, silica and chromium oxide in which the atomic ratio of Fe to Si to Cr is 100 : 0.1 – 5 : 0.1 – 5, preferably 100 : 0.1 – 3 : 0.1 – 3.

The catalyst used in this invention as defined above is superior over the conventional catalysts used in the ortho-alkylation of phenol compounds, in selectivity, ield and durability of activity. The catalyst (b) is somewhat more preferred than the catalyst (a) since it exhibits a better durability of activity than the catalyst (a).

The catalysts used in this invention can be prepared by any methods known per se, such as (a) a co-precipitation method, (b) a gel-kneading method, or (c) a method involving kneading gel and a metal salt. Of these, the co-precipitation method is especially preferred. One example of preparing the catalyst of this invention using the co-precipitation method will be described specifically in the following.

Preparation of the catalyst (a)

A silicon compound is added in a predetermined amount to an aqueous solution of an iron salt at a temperature of 10° to 100°C. with stirring, and an alkali agent is added dropwise to adjust the pH to 6 – 8. Stirring is further continued to complete the reaction, and thereby to obtain a precipitate of a hydrogel. The resulting precipitate is thoroughly washed with water, filtered, pre-dried at 100° to 200°C., and calcined at 350° to 700°C., preferably at 400° to 600°C. for 3 to 15 hours in a stream of air.

Preparation of the catalyst (b)

While an aqueous solution containing the required amounts of an iron salt, a silicon compound and a chromium salt is stirred at a temperature of 10° to 100°C., an alkali agent is added to adjust the pH to 6 – 8. Stirring was further continued to complete the reaction and thereby to form a precipitate of a hydrogel. The resulting precipitate is thoroughly washed with water, filtered, pre-dried at 100° to 200°C., and then calcined 350° to 700°C., preferably 400° to 600°C. for 3 to 15 hours in a stream of air.

In any of the above procedures for preparing the catalyst, the iron salt to be used may, for example, be ferric nitrate, ferric sulfate, ferric chloride, ferrous nitrate, ferrous sulfate, and ferrous chloride. The ferric nitrate is especially preferred.

Examples of suitable silicon compounds are inorganic silicon compounds such as sodium silicate or silica sol, and organic silicon compounds such as ethyl ortho-silicate.

Examples of suitable chromium compounds are trivalent chromium salts such as chromium nitrate, chromium sulfate or chromium chloride. Chromic acid salts and perchromic acid salts are also used.

Examples of suitable alkali agents are ammonia, urea, and hydroxides of metal elements of group IA of the periodic table such as sodium hydroxide. Ammonium is especially preferred.

In the performance of the ortho-alkylation method of this invention, the suitable mol ratio of the phenol compound fed to the alcohol fed is 1 : 1 – 10. Inert diluent gases such as steam or nitrogen gas may be incorporated in the feed gaseous mixture. Especially when steam is incorporated in a proportion of 1 to 10 mols per mol of the phenol compounds, the rate of recovery of the unreacted alcohol can be increased, and the reduction of the activity of the catalyst can be inhibited.

The reaction temperature employed in the process of this invention is 300° to 450°C., preferably 320° to 400°C. The reaction pressure may be any of atmospheric pressure, an elevated pressure, or a reduced pressure. When the elevated pressures are employed, it is suitably 0.5 to 40 Kg/cm².G.

After the reaction, the resulting reaction product is condensed or caused to be absorbed by an organic solvent, and then separated by, for example, distillation, thereby to afford the desired product.

The present invention makes it possible to obtain ortho-alkylated phenols in a high yield not attainable heretofore and at high conversion and selectivity while inhibiting side-reactions, and the activity of the catalyst can be maintained for very long periods of time.

The catalysts used in this invention have a very long active lifetime, and can be easily regenerated even when the activity is reduced after use for long periods of time.

The process of this invention is commercially advantageous especially as methods for producing 2,6-xylenol from phenol or ortho-cresol and methanol.

The following Examples illustrate the present invention more specifically.

EXAMPLES 1 TO 6 AND COMPARATIVE EXAMPLES 1 TO 2

300 g of ferric nitrate enneahydrate was dissolved in 3 liters of water, and with stirring at 85°C., a predetermined amount of water glass No. 3 (30% aqueous solution) was added after dilution with water. Then, 10% aqueous ammonia was slowly added dropwise, and when the pH of the solution became 7.0, the addition of the aqueous ammonia was stopped, followed by further stirring for 1 hour. The resulting gel-like precipitate was thoroughly washed with water, filtered, and then dried at 180°C. for 10 hours. The dried gel was pulverized to a size of 6 to 10 mesh, and calcined at 470°C. for 3 hours in a stream of air to form a catalyst. The catalyst had the composition shown in Table 1.

40 ml. of the catalyst was packed into a stainless steel reaction tube. A mixture of methanol and phenol in a molar ratio of 5:1 was gasified, and passed together with 30 ml./min. nitrogen gas through the catalyst layer held at 350°C. at a liquid hourly space velocity (LHSV) of 0.6 Kg/l.hr. The results of the reaction were as shown in Table 1.

For comparison, the procedure of Examples 1 to 6 was repeated using a catalyst prepared in the same manner as above from ferric nitrate enneahydrate alone (Comparative Example 1) and a silica gel catalyst having a purity of more than 99% and prepared from silica sol (Comparative Example 2). The results are also shown in Table 1.

Table 1

| | | Comparative Example 1 | 1 | 2 | Examples 3 | 4 | 5* | 6* | Comparative Example 2 |
|---|---|---|---|---|---|---|---|---|---|
| Catalyst | $Fe_2O_3/SiO_2$ (molar ratio) | 100/0 | 100/0.34 | 100/1.32 | 100/3.50 | 100/20 | 100/50 | 100/100 | 0/100 |
| | Fe/Si (atomic-ratio) | 100/0 | 100/0.17 | 100/0.66 | 100/1.75 | 100/10 | 100/25 | 100/50 | 0/100 |

Table 1-continued

| | | Compara-tive Example 1 | 1 | 2 | Examples 3 | 4 | 5* | 6* | Compara-tive Example 2 |
|---|---|---|---|---|---|---|---|---|---|
| Conversion of phenol (mol %) | | 10.0 | 98.6 | 100 | 100 | 100 | 99.7 | 99.0 | 0.57 |
| Selectivity (mol %) | Anisole | 0.04 | 0.03 | 0.04 | 0.10 | 0.49 | 0.25 | 0.05 | 67.4 |
| | o-Cresol | 82.6 | 4.98 | 1.14 | 1.84 | 2.71 | 0.72 | 54.5 | 14.9 |
| | 2,6-Xylenol | 17.1 | 93.2 | 96.7 | 94.5 | 81.4 | 90.7 | 39.0 | 14.6 |
| | 2,4,6-Tri-methylphenol | — | 0.92 | 1.17 | 1.98 | 10.34 | 4.98 | 3.04 | 1.78 |

*The catalyst used in Examples 5 and 6 was prepared in the same manner as described above except using silica sol (20% aqueous solution) instead of the water glass No. 3.

EXAMPLE 7

In order to examine the lifetime of the catalyst of this invention, a mixture of methanol and phenol at a molar ratio of 5 : 1 was passed through the catalyst layer at an LHSV of 0.6 Kg/l.hr. and reacted at 350°C. for long hours. The results are shown in Table 2.

Table 2

| Reaction time (hours) | Conversion of phenol (mol%) | Selectivity (mol%) | | |
|---|---|---|---|---|
| | | o-Cresol | 2,6-Xylenol | 2,4,6-Trimethyl phenol |
| 4 | 100 | 0.97 | 96.5 | 1.70 |
| 20 | 100 | 1.66 | 96.5 | 0.89 |
| 40 | 100 | 3.78 | 94.6 | 0.70 |
| 60 | 100 | 3.42 | 94.9 | 0.69 |
| 80 | 100 | 4.61 | 93.9 | 0.56 |
| 100 | 100 | 6.01 | 92.9 | 0.52 |
| 150 | 100 | 6.60 | 91.9 | 0.49 |

EXAMPLES 8 TO 10

Example 3 was repeated except that each of the phenol compounds indicated in Table 3 was used instead of the phenol. The results are shown in Table 3.

Table 3

| Examples | Phenol Compounds | Conversion (mol%) | Selectivity of the products (mol%) | |
|---|---|---|---|---|
| 8 | o-Cresol | 98.2 | 2,6-Xylenol | 97.6 |
| | | | 2,4,6-Trimethylphenol | 1.55 |
| 9 | o-Ethylphenol | 98.6 | 2-Methyl-6-ethylphenol | 87.4 |
| | | | 2-Ethyl-4-methylphenol | 1.63 |
| 10 | p-Ethylphenol | 98.8 | 2-Methyl-4-ethylphenol | 27.2 |
| | | | 2,6-Dimethyl-4-ethylphenol | 69.6 |

EXAMPLES 11 TO 13

Using the catalyst of Example 2, phenol was reacted with each of the various alcohols shown in Table 4. The molar ratio of the alcohol to the phenol was 5 : 1, the LHSV was 0.6 Kg/l.hr, and the temperature of the catalyst layer was 380°C. The results are shown in Table 4.

Table 4

| Examples | Alcohols | Conversion of phenol (mol%) | Selectivity (mol%) | | |
|---|---|---|---|---|---|
| | | | o-Alkyl phenol | 2,6-Di-alkyl phenol | Ortho-substitution selectivity |
| 11 | Ethanol | 89.5 | 67.2 | 25.2 | 92.4 |
| 12 | n-Propanol | 64.3 | 90.9 | 2.99 | 93.9 |
| 13 | n-Butanol | 71.9 | 87.5 | 2.70 | 90.2 |

EXAMPLES 14 AND 14

In Example 14, a catalyst (b) of this invention was prepared in the following way.

300 g of ferric nitrate enneahydrate and 2.97 g of chromium nitrate enneahydrate was dissolved in 3 liters of water, and with stirring at room temperature, 1.65 g of water glass No. 3 (SiO₂ content 30%) was after dilution with water. With continued stirring, 10% aqueous ammonia was slowly added dropwise. When the pH of the solution became 7.0, the addition of aqueous ammonia was stopped. Stirring was further performed for 1 hour, and the resulting gel was aged. Then, the precipitate was filtered, washed with water, and pre-dried at 180°C. for 10 hours. The dried gel was pulverized to a size of 6 to 10 mesh, and calcined at 470°C. for 7 hours in a stream of air. The composition of the catalyst obtained was: $Fe_2O_3 : SiO_2 : Cr_2O_3 = 100 : 2 : 1$ (molar ratio).

In Example 15, a catalyst (a) of this invention was prepared under the same conditions as above except that the chromium nitrate was not used. The composition of the resulting catalyst was : $Fe_2O_3: SiO_2 = 100 : 2$ (molar ratio).

Phenol was alkylated with methyl alcohol for long hours using the above catalysts.

The reaction conditions were as follows:

40 ml. of the catalyst was filled in a stainless steel reaction tube, and a gaseous mixture of methanol and phenol (5/1 molar ratio) was passed together with 30 ml./min. of nitrogen gas through the catalyst layer held at 350° to 355°C. at an LHSV of 0.6 Kg/l.hr for long hours.

The results obtained are shown in Table 5.

Table 5

| | Example 14 | | | | Example 15 | | | |
|---|---|---|---|---|---|---|---|---|
| Catalyst | Fe$_2$O$_3$:SiO$_2$:Cr$_2$O$_3$ (mol ratio) = 100:2:1 | | | | Fe$_2$O$_3$:SiO$_2$ (mol ratio) = 100:2 | | | |
| | Fe:Si:Cr (atomic ratio) = 100:1:1 | | | | Fe:Si (atomic ratio) = 100:1 | | | |
| | | Yield (mol%) | | | | Yield (mol%) | | |
| Reaction time (hours) | Conversion of phenol (mol%) | o-Cresol | 2,6-Xylenol | 2,4,6-Tri-methyl-phenol | Conversion of phenol (mol%) | o-Cresol | 2,6-Xylenol | 2,4,6-Tri-methyl-phenol |
| 4 | 100 | 0.30 | 96.7 | 1.58 | 100 | 0.97 | 96.0 | 1.70 |
| 40 | 100 | 1.05 | 97.3 | 0.73 | 100 | 3.78 | 94.6 | 0.70 |
| 80 | 100 | 1.37 | 97.0 | 0.71 | 100 | 4.61 | 93.9 | 0.56 |
| 120 | 100 | 2.52 | 95.9 | 0.67 | 100 | 6.40 | 92.2 | 0.50 |
| 160 | 100 | 2.70 | 95.7 | 0.66 | 99.7 | 6.60 | 91.9 | 0.49 |
| 200 | 100 | 3.51 | 94.9 | 0.64 | 99.4 | 13.24 | 84.6 | 0.41 |
| 240 | 100 | 4.13 | 94.3 | 0.63 | 97.6 | 22.50 | 74.0 | 0.54 |
| 280 | 100 | 2.85 | 95.5 | 0.66 | | | | |
| 320 | 100 | 4.85 | 93.5 | 0.67 | | | | |
| 360 | 100 | 5.97 | 92.4 | 0.66 | | | | |
| 400 | 100 | 6.23 | 92.1 | 0.69 | | | | |

EXAMPLES 16 TO 17

In the same way as in Example 14, a catalyst having an Fe$_2$O$_3$/SiO$_2$/Cr$_2$O$_3$ molar ratio of 100/2/0.5 and a catalyst having an Fe$_2$O$_3$/SiO$_2$/Cr$_2$O$_3$ molar ratio of 100/2/3 were prepared, and using these catalysts the reaction was performed under the same conditions as in Example 14 for long hours. The results are shown in Table 6.

Table 6

| | Example 16 | | | | Example 17 | | | |
|---|---|---|---|---|---|---|---|---|
| Catalyst | Fe$_2$O$_3$:SiO$_2$:Cr$_2$O$_3$ (molar ratio) = 100:2:0.5 | | | | Fe$_2$O$_3$:SiO$_2$Cr$_2$O$_3$ (molar ratio) = 100:2:3 | | | |
| | Fe:Si:Cr (atomic ratio) = 100:1:0.5 | | | | Fe:Si:Cr (atomic ratio)=100:1:3 | | | |
| | | Yield (mol%) | | | | Yield (mol%) | | |
| Reaction time (hours) | Conversion of phenol (mol%) | o-Cresol | 2,6-Xylenol | 2,4,6-Tri-methyl-phenol | Conversion of phenol (mol%) | o-Cresol | 2,6-Xylenol | 2,4,6-Tri-methyl-phenol |
| 4 | 100 | 1.14 | 95.4 | 1.85 | 100 | 4.40 | 91.8 | 1.12 |
| 30 | 100 | 1.77 | 95.7 | 1.17 | 99.8 | 6.21 | 91.0 | 1.30 |
| 60 | 100 | 1.79 | 95.2 | 1.15 | 99.5 | 5.46 | 91.9 | 0.96 |
| 90 | 100 | 4.97 | 93.5 | 0.97 | 99.6 | 7.22 | 90.3 | 1.00 |
| 120 | 100 | 5.47 | 93.0 | 0.97 | 98.9 | 8.76 | 88.2 | 0.96 |
| 150 | 100 | 6.08 | 92.4 | 0.96 | 98.0 | 9.50 | 87.5 | 0.91 |
| 180 | 100 | 6.50 | 92.0 | 0.96 | | | | |
| 210 | 100 | 6.65 | 91.4 | 0.94 | | | | |
| 230 | 99.7 | 8.69 | 90.0 | 0.91 | | | | |

COMPARATIVE EXAMPLES 3 AND 4

Using an iron oxide-chromium oxide catalyst prepared in the same way as in Example 14 from ferric nitrate enneahydrate and chromium nitrate enneahydrate, the reaction was carried out in the same way as in Example 14. The composition of the catalyst obtained and the results of the reaction are shown in Table 7.

Table 7

| | Comparative Example 3 | | | | Comparative Example 4 | | | |
|---|---|---|---|---|---|---|---|---|
| Catalyst | Fe$_2$O$_3$:Cr$_2$O$_3$=100:1 (molar ratio) | | | | Fe$_2$O$_3$:Cr$_2$O$_3$=100:5 (molar ratio) | | | |
| | | Yield (mol%) | | | | Yield (mol%) | | |
| Reaction time (hours) | Conversion of phenol (mol%) | o-Cresol | 2,6-Xylenol | 2,4,6-Tri-methyl-phenol | Conversion of phenol (mol%) | o-Cresol | 2,6-Xylenol | 2,4,6-Tri-methyl-phenol |
| 4 | 68.3 | 55.5 | 12.3 | 0.07 | 64.9 | 40.4 | 23.8 | 0.19 |
| 30 | 78.3 | 59.2 | 18.5 | 0.13 | 49.9 | 28.3 | 21.1 | 0.16 |
| 60 | 76.6 | 59.3 | 16.9 | 0.14 | 30.2 | 14.8 | 14.9 | 0.19 |
| 90 | 76.5 | 59.0 | 16.7 | 0.14 | 23.8 | 10.9 | 12.5 | 0.18 |

What we claim is:

1. A process for alkylating the orthoposition of a phenol compound of the formula

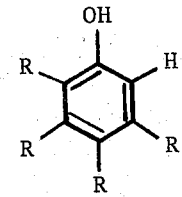

wherein R's may be the same or different, and each represents a monovalent substituent such as a hydrogen atom, an alkyl group of 1 to 6 carbon atoms, or a phenyl group,
which comprises bringing a phenol compound containing at least one hydrogen atom at its ortho-position and a lower saturated aliphatic alcohol containing 1 to 4 carbon atoms into contact with a catalyst in the gaseous phase at a pressure of atmospheric to 40 Kg/cm$^2$.G and at a temperature of 300° to 450°C, said catalyst being selected from the group consisting of
 a. a mixture of iron oxide and silica in which the atomic ratio of Fe to Si is 100 : 0.03 – 200, and
 b. a mixture of iron oxide, silica and chromium oxide in which the atomic ratio of Fe to Si to Cr is 100 : 0.1 – 5 : 0.1 – 5.

2. The process of claim 1 wherein the atomic ratio of Fe : Si of the catalyst (a) is 100 : 0.1 – 50.

3. The process of claim 1 wherein the atomic ratio of Fe : Si : Cr of the catalyst (b) is 100 : 0.1 – 3 : 0.1 – 3.

4. The process of claim 1 wherein the phenol compound is phenol, cresol, xylenol, or ethylphenol.

5. The process of claim 1 wherein said alcohol is methanol.

6. The process of claim 1 wherein the molar ratio of said phenol compound to said alcohol is 1 : 1 – 10.

7. The process of claim 1 wherein the contacting between said phenol compound and said alcohol is carried out in the presence of an inert diluting gas.

8. The process of claim 1 wherein said diluting gas is steam, and the proportion of the steam is 1 to 10 mols per mol of the phenol compound.

* * * * *

UNITED STATES PATENT AND TRADEMARK OFFICE
CERTIFICATE OF CORRECTION

PATENT NO. : 3,953,529
DATED : April 27, 1976
INVENTOR(S) : YONEMITSU, ET AL.

It is certified that error appears in the above-identified patent and that said Letters Patent are hereby corrected as shown below:

Item 30, line 3, delete "48-01894", insert -- 48-91894 --

Claim 1, line 1, delete "orthoposition", insert -- ortho-position --

Signed and Sealed this

Twentieth Day of July 1976

[SEAL]

Attest:

RUTH C. MASON
*Attesting Officer*

C. MARSHALL DANN
*Commissioner of Patents and Trademarks*